United States Patent [19]

Rhodes et al.

[11] Patent Number: 4,495,284

[45] Date of Patent: Jan. 22, 1985

[54] MICROBIOLOGICAL PROCESS FOR THE PREPARATION OF 1-CARVONE

[75] Inventors: Peter M. Rhodes, Margate; Norman Winskill, Ramsgate, both of England

[73] Assignee: Pfizer Inc., New York, N.Y.

[21] Appl. No.: 443,805

[22] Filed: Nov. 22, 1982

Related U.S. Application Data

[63] Continuation-in-part of Ser. No. 418,893, Sep. 16, 1982, abandoned.

[30] Foreign Application Priority Data

Oct. 21, 1981 [GB] United Kingdom ................ 8131667

[51] Int. Cl.$^3$ .......................... C12P 7/26; C12N 1/20; C12R 1/38

[52] U.S. Cl. .................................... 435/148; 435/253; 435/874

[58] Field of Search ........................ 435/148, 253, 874

[56]  References Cited

FOREIGN PATENT DOCUMENTS 77682  4/1983  European Pat. Off. ............ 435/148
124388  9/1981  Japan ................................... 435/874

Primary Examiner—Esther M. Kepplinger
Attorney, Agent, or Firm—Charles J. Knuth; James H. Monroe

[57]  ABSTRACT

A process for the preparation of 1-carvone (spearmint flavor) comprises cultivating a carvone producing microorganism of the genus Pseudomonas in an aqueous nutrient media in the presence of 1-$\alpha$- or 1-$\beta$-pinene.

5 Claims, No Drawings

MICROBIOLOGICAL PROCESS FOR THE PREPARATION OF l-CARVONE

CROSS REFERENCE TO RELATED APPLICATIONS

This application is a continuation in part of co-pending application Ser. No. 418,893 filed Sept. 16, 1982, now abandoned.

BACKGROUND OF THE INVENTION

This invention relates to the preparation of l-carvone from 1-α- or 1-β-pinene by microbiological means.

l-Carvone, a ketonic terpene, is a major constituent of spearmint oil and is an important flavoring substance that is widely used for example, in chewing gum, toothpaste, toiletries and in food and drinks.

In the past l-carvone has either been isolated from natural spearmint oil or manufactured by complex synthetic chemical reactions, for example as described in U.S. Pat. No. 2,796,428. A number of attempts have also been described to obtain l-carvone by microbiological means. Thus in Japanese published patent application No. 47-38998 a process is described for the preparation of carvone from limonene using an organism belonging to the genus Corynebacteria. The degradation of α-pinene by bacteria has been described in *Fermentation Technology Today* (1972) 609; however, although a number of terpenoid degradation products were identified, including in particular cis-thujone and trans-carveol, there is no suggestion that l-carvone may be produced by this process.

SUMMARY OF THE INVENTION

We have now isolated a new organism of the genus Pseudomonas which we have found to be capable of oxidising 1-α-pinene or 1-β-pinene directly to 1-carvone. Both 1-α-pinene and 1-β-pinene occur as principal constituent of certain naturally occurring turpentine oils and are consequently cheap and readily available starting materials.

Thus according to the present invention, there is provided a microbiological process for the preparation of l-carvone from 1-α- or 1-β-pinene. In particular the invention provides a process for the preparation of l-carvone which comprises cultivating an l-carvone producing microoganism of the genus Pseudomonas in an aqueous nutrient medium in the presence of 1-α-pinene or 1-β-pinene and recovering the l-carvone from the fermentation medium.

The process is preferred wherein the microorganism is Pseudomonas strain NCIB 11671, wherein the cultivation is performed at a temperature of about 28° C. and a pH of from about 6.8 to 7.0, wherein the 1-α- or 1-β-pinene is present as the only carbon source and wherein the l-carvone produced is recovered by extraction with a water-immiscible organic solvent.

An isolated and biologically pure microorganism of the genus Pseudomonas strain NC1B no. 11671 and mutants thereof, said strain being characterized as capable of converting 1-α- or 1-β-pinene to l-carvone when cultured under aerobic conditions in an aqueous nutrient medium comprising assimilable sources of nitrogen and essential mineral salts, in the presence of 1-α-pinene or 1-β-pinene is also a part of this invention.

DETAILED DESCRIPTION OF THE INVENTION

The l-carvone producing organism of the present invnetion was isolated from a sewage sample and was deposited with the National Collection of Industrial Bacteria (NCIB) P.O. Box 31, 135 Abbey Road, Aberdeen, AB9 8DG, Scotland on 13th July, 1981, as Deposit No. 11671. The bacillus is identified as a new strain belonging to the genus Pseudomonas and a description of the properties of the microorganism in accordance with Bergey's Manual of Determinative Bacteriology, 8th Edition, editors R. E. Buchan and N. E. Gibbons is given below:

Cell morphology (Oxoid CM3 Nutrient Agar, 30° C.) Gram-negative, rod-shaped cells, 0.8×c. 2.4. to c. 4.8 μm in exponential phase, short rods at 2 days, motile by 1 to 4 polar Flagella.

Colonial morphology (CM3, 30° C., 2 days). Colonies circular, convex, entire smooth and shiny, semitranslucent, c. 0.1 mm at 24 hours and 1 mm at 2 days, slightly yellow at 2 days and pale yellow at 7 days.

Physiology. Growth occurred under the following conditions, at 25° C. except as stated: on CM3 from 10° C. to 41° C. but not at 5° C. and 45° C.; at pH 7.4 (CM3); at 0.03 M $Na^+$ but not at 0.83 M $Na^+$ (CM1+4.5% NaCl) (carbon source utilization medium, see below): with $NH_4^+$ as sole nitrogen source in a mineral salts medium with glucose or other sole carbon sources, without growth factors.

Growth was resistant to penicillin 4 units, streptomycin 25 μg 2,4-diamino-6,7-diisopropylpteridine phosphate 35 μg and sensitive to chloramphenicol 50 μg, tetracycline 25 μg, novobiocin μg and polymyxin B 250 units (discs on CM3, 25° C.).

Biochemical reactions (25° C. except as stated)

Positive: Catalase (30° C.); gelatin hydrolysis; orthonitrophenyl-β-galactopyranoside; ammonia from tryptone water (weak).

Negative: Fermentative attack on glucose (30° C.); poly-β-hydroxybutyrate accumulation as an intracellular carbon reserve (presumed from nonutilization of DL-β-hydroxybutyrate, Bergey's Manual p. 219); autotrophic growth in an atmosphere of $H_2$, $CO_2$ and $O_2$; fluorescent pigments; pyocyanin; arginine 'dihydrolase', Moller's; lysine decarboxylase, Moller's; ornithine decarboxylase, Moller's; nitrite from nitrate; nitrogen from nitrate; deoxyribonuclease; gelatin stab liquefaction (28 days at 20° C.); casein hydrolysis; starch hydrolysis; egg yolk lecithinase; egg yolk lipase; Tween (trade mark) 80 hydrolysis; urease; hydrogen sulphide from triple sugar iron medium; indole production; methyl red; Voges-Proskauer (acetylmethylcarbinol production); acid from glucose/peptone/water/sugar; gas from glucose/peptone/water/sugar; levan from sucrose.

Carbon Source Utilization

Compounds listed in the tables for Pseudomonas in Bergey's Manual of Determinative Bacteriology 1974 and in the order for Pseudomonas in R. Y. Stanier et. al. (1966) *J. gen. Microbiol.* 43, 159. (Medium of N. J. Palleroni & M. Doudoroff (1972) *A. Rev. Phytopathol.* 10, 73, as broth, slightly modified.)

Positive:

D-xylose; L-arabinose; L-rhamnose; D-glucose; D-fructose; sucrose; cellobiose; acetate; propionate; butyrate; DL-lactate; ethanol; para-hydroxybenzoate; β-alanine; L-histidine.

Negative:

D-Ribose; saccharate; malonate; D(−)-tartrate; meso-tartrate; DL-β-hydroxybutyrate; glycollate; levulinate; citraconate; mesaconate; erythritol; sorbitol; meso-inositol; adonitol; propylene glycol; 2,3-butylene glycol; methanol; geraniol; meta-hydroxybenzoate; testosterone; L-valine; L-arginine; benzylamine; betaine; pantothenate.

It is to be understood that the invention includes the use of any mutants produced from this microorganism by various means such as by irradiation with X-rays or ultraviolet light, or treatment with nitrogen mustards and the like mutagenic reagents, provided such mutants are capable of producing l-carvone from 1-α- or 1-β-pinene. The l-carvone producing ability of any strain of microorganism for the present invention can be readily determined by cultivating the organism in the presence of 1-α- or 1-β-pinene in accordance with the description and examples contained herein, and detecting l-carvone in the substrate by subjecting a sample of the substrate to chromatographic analysis.

The aqueous fermentation medium used in the present formation invention may contain various carbon sources such as carbohydrates (glucose, glycerol, starch, sucrose, etc.) or hydrocarbons (e.g. n-alkanes) in addition to 1-α- or 1-β-pinene. However for maximum l-carvone production it is preferred that 1-α- or 1-β-pinene is used as the major or only carbon source. Other nutrients which must be included are sources of assimilable nitrogen and inorganic salts. Many nitrogen sources are suitable such as ammonium sulphate, ammonium chloride, sodium or potassium nitrate, urea, amino acids, peptones and other digested proteins. Trace essential minerals and vitamins may be added to the medium if desired.

Inorganic elements, particularly phosphorus (supplied for example as phosphate salts), magnesium (which may be supplied as magnesium sulphate), sulphur (supplied as sulphate salts), potassium and sodium, must be provided, either as salts, or as components of complex medium ingredients which contain them as impurities. Trace elements such as calcium, iron, manganese, zinc, copper, cobalt and molybdenum may be supplied in the same way.

The Pseudomonas Sp strain can be cultured at temperatures from 22° to 36° C. at a pH in the range from 6.5 to 7.8 and significant yields of l-carvone are obtained after fermentation for from 1 to 3 days.

An inoculum of the organism is prepared by transferring cells of the strain grown on a suitable medium, such as nutrient agar, to an aqueous nutrient medium containing 1-α- or 1-β-pinene and a carbohydrate in a shake flask. After shaking and incubating for a sufficient time at a suitable temperatures (for example for 24 hours at 28° C.), aliquots of this inoculum are then transferred to similar sterile media in fermenters which are stirred and aerated by forcing compressed air through the mixture. The pH of the medium is maintained at a suitable level, preferably between 6.8 and 7.0, by addition of alkali, for example by adding an aqueous solution of sodium hydroxide or ammonia.

When significant quantities of l-carvone have accumulated in the fermentation medium, as shown by analysis of samples for example using gas-liquid chromatography, the product is recovered from the media by methods well-known in the art for the recovery of water-insoluble organic liquids. Thus extractions of the culture broth with a water immiscible organic solvent, centrifugation to separate the organic and aqueous phases, drying the organic phase, and distillation to remove the solvent and any residual pinene yields the product in crude form. Suitable solvents for the extraction include carbon tetrachloride, dichloromethane, diethylether, etc.

Further purification of the crude product may be achieved, if desired, using standard techniques, for example by using chromatography or fractional distillation under reduced pressure.

The invention is illustrated by the following examples:

EXAMPLE 1

The same medium was used in all the Examples, except as stated otherwise. This consisted of disodium hydrogen orthophosphate dihydrate 3.04 grams, dipotassium hydrogen orthophosphate 5.31 grams, and ammonium sulphate 0.5 grams, dissolved in distilled water to give 1 liter volume. This was sterilized at 120° C. for 15 minutes. After cooling to 20° C., 2 ml of a sterile solution of the following composition was added aseptically: calcium carbonate 2.5 grams, zinc oxide 0.5 grams, ferrous sulphate heptahydrate 7.0 grams, manganous chloride dihydrate 1.25 grams, cuprous chloride dihydrate 0.2 grams, cobaltous chloride hexahydrate 0.3 grams, boric acid 0.1 grams, hydrochloric acid 9.7 ml of a 10 molar solution, distilled water to give a volume of 1 liter. The solution was sterilized by filtration.

20 ml. of the sterile medium was added to a sterilized 300 ml Erlenmayer flask fitted with an aluminum foil-covered rubber bung. To this was added as carbon source filter-sterilized 1-α-pinene 0.1 ml. The flask was inoculated with 4 ml of a 24 hour 1-α-pinene grown culture of Pseudomonas NCIB No. 11671. Three identical flasks were prepared simultaneously and placed on a rotary shaker at 28° C. and shaken at 220 rpm for 24, 48, and 72 hours. After the desired period the culture was extracted with 20 ml diethyl ether. The ether layer was separated and a sample subjected to gas-liquid chromatography. A peak with the same retention time as authentic l-carvone was observed, and when the area was compared with that of a standard carvone solution the concentrations in the culture at various times were estimated to be: 24 hours 5.6 mg/liter, 48 hours 13.4 mg/liter, 72 hours 2.7 mg/liter. The identity of the product was confirmed by GC-mass spectroscopy by comparison with an authentic sample of l-carvone.

EXAMPLE 2

In the following procedure the ammonium sulphate concentration of the medium was increased to 2.0 g/liter. A three liter total volume fermenter containing 2 liters of medium, was sterilized, 10 ml 1-α-pinene was added and 1-α-pinene was also continuously pumped into the vessel at a rate of 1 ml/hour throughout the process. Air was added at 200 ml/hour, and the culture stirred at 1000 rpm. The temperature was controlled at 28° C., and the pH was controlled between 6.8 and 7.0 by the automatic addition of a 5% solution of ammonium hydroxide. The vessel was inoculated with 200 ml of a 48 hour old culture of Pseudomonas 11671 grown on 1-α-pinene. Further additions of 1-α-pinene were made at the following times after inoculation: 0 hours (10ml), 17.5 hours (10 ml), 21 hours (10 ml) and 22½ hours (20 ml). Maximum carvone formation was observed after 24.5 hours, when a concentration of 8.2 mg/liter carvone was measured by gas chromatography.

EXAMPLE 3

In this example the ammonium sulphate concentration in the medium was 4 grams/liter. 50 Liters of sterile medium was prepared in a 75 liter total volume fermenter. The medium was aerated at 5 liters/minute, and agitated at 450 rpm. The temperature was controlled at 28° C. and the pH was controlled at 6.8 by the automatic addition of a 10% by weight solution of sodium hydroxide. 1-α-Pinene (250 ml) was added and the fermenter was inoculated with 2400 ml of Pseudomonas NCIB no. 11671, 48 hour culture. Further additions of pinene were made as follows; 0 hours (250 ml), 3 hours (750 ml), 8 hours (500 ml), 19 hours (250 ml) and 23 hours (250 ml). Carvone production was followed by gas chromatography of ether extracts or broth samples. After 25 hours 7.4 mg/liter carvone had been produced, and the fermentation was stopped. Carbon tetrachloride (9 liters) was added to the fermenter, and stirred at 450 rpm for 15 minutes. The agitator was turned off, and the liquid was allowed to stand overnight. The organic layer was separated and evaporated to a volume of 8 cc estimated to contain 64 mg 1-carvone by glc. Purification by preparative gas chromatography and preparative thin-layer chromatography gave 1-carvone (2.4 mg) >99% pure by gas liquid chromatography. Nuclear magnetic resonance spectra identical with published spectra; optical rotation: $[\alpha]_{589}^{20} = -48°$ (literature $-62.5°$ i.e. 89% optically pure 1-isomer).

EXAMPLE 4

A fermentation is performed as described in Example 3 but using 1-β-pinene to yield 1-carvone in an identical manner.

We claim:

1. A process for the preparation of 1-carvone which comprises cultivating the carvone producing microoorganism Pseudomonas strain NCIB no. 11671 in an aqueous nutrient medium in the presence of 1-α-pinene or 1-β-pinene and recovering 1-carvone from the fermentation medium.

2. A process according to claim 1 wherein the cultivation is performed at a temperature of about 28° C. and a pH of from about 6.8 to 7.0.

3. A process according to claim 1 wherein the 1-α- or 1-β-pinene is present as the only carbon source.

4. A process according to claim 1 wherein the 1-carvone produced is recovered by extraction with a water-immiscible organic solvent.

5. An isolated and biologically pure microorganism of the genus Pseudomonas strain NCIB no. 11671 and mutants thereof, said strains being characterized as capable of converting 1-α- or 1-β-pinene to 1-carvone when cultured under aerobic conditions in an aqueous nutrient medium comprising assimilable sources of nitrogen and essential mineral salts, in the presence of 1-α-pinene or 1-β-pinene.

* * * * *